(12) United States Patent
Pedersen et al.

(10) Patent No.: US 8,506,514 B2
(45) Date of Patent: Aug. 13, 2013

(54) SYSTEM FOR REGULATING INTRACRANIAL PRESSURE

(75) Inventors: Hans Joergen Pedersen, Harrislee (DE); Arne Briest, Karlsruhe (DE)

(73) Assignee: Neckarate GmbH & Co. KG, Oberstenfeld (DE)

( * ) Notice: Subject to any disclaimer, the term of this patent is extended or adjusted under 35 U.S.C. 154(b) by 0 days.

(21) Appl. No.: 13/054,309

(22) PCT Filed: Jul. 14, 2009

(86) PCT No.: PCT/DK2009/000173
§ 371 (c)(1),
(2), (4) Date: May 25, 2011

(87) PCT Pub. No.: WO2010/006609
PCT Pub. Date: Jan. 21, 2010

(65) Prior Publication Data
US 2011/0224595 A1    Sep. 15, 2011

(30) Foreign Application Priority Data

Jul. 18, 2008  (DK) ................................. 2008 01014

(51) Int. Cl.
*A61M 37/00* (2006.01)

(52) U.S. Cl.
USPC ....................................................... 604/6.16

(58) Field of Classification Search
USPC .................... 604/6.16; 607/60; 128/903
See application file for complete search history.

(56) References Cited

U.S. PATENT DOCUMENTS

| 4,385,636 | A | | 5/1983 | Cosman |
| 5,355,714 | A | * | 10/1994 | Suzuki et al. ............... 73/146.5 |
| 5,704,352 | A | | 1/1998 | Tremblay et al. |
| 6,083,174 | A | * | 7/2000 | Brehmeier-Flick et al. .. 600/561 |
| 6,248,080 | B1 | * | 6/2001 | Miesel et al. ................. 600/561 |
| 6,868,739 | B1 | * | 3/2005 | Krivitski et al. ........... 73/861.05 |
| 2002/0026138 | A1 | | 2/2002 | Cowan, Jr. et al. |
| 2002/0161304 | A1 | | 10/2002 | Eide |
| 2004/0068201 | A1 | | 4/2004 | Saul |
| 2004/0082900 | A1 | | 4/2004 | Luttich |
| 2004/0236300 | A1 | * | 11/2004 | Gibbs et al. .............. 604/385.24 |
| 2005/0020962 | A1 | * | 1/2005 | Reich et al. ....................... 604/8 |
| 2005/0137652 | A1 | | 6/2005 | Cauller et al. |

FOREIGN PATENT DOCUMENTS

| DE | 19541377 A1 | 6/1996 |
| DE | 202006004445 U1 | 5/2006 |
| EP | 1050264 A1 | 8/2000 |
| WO | 03057016 A2 | 7/2003 |
| WO | 03096889 A1 | 11/2003 |

OTHER PUBLICATIONS

International search report for PCT/DK2009/000173 dated Sep. 10, 2009.

\* cited by examiner

*Primary Examiner* — Leslie Deak
*Assistant Examiner* — Jordan B Bailey
(74) *Attorney, Agent, or Firm* — McCormick, Paulding & Huber LLP (57) ABSTRACT

The present invention relates to a method and system to regulate pressure in an object, and is especially suitable for regulating intracranial pressure in people suffering from hydrocephalus. The system includes the measurement of physical parameters other than the pressure to be regulated, especially the present position of the object, such as the inclination.

14 Claims, 7 Drawing Sheets

SYSTEM FOR REGULATING INTRACRANIAL PRESSURE

CROSS REFERENCE TO RELATED APPLICATIONS

This application is entitled to the benefit of and incorporates by reference essential subject matter disclosed in International Patent Application No. PCT/DK2009/000173 filed on Jul. 14, 2009, Danish Patent Application No. PA 2008 01014 filed on Jul. 18, 2008.

FIELD OF THE INVENTION

The present invention relates to a method and system to regulate pressure in an object, and is especially suitable for regulating intracranial pressure in people suffering from hydrocephalus. The system includes the measurement of physical parameters other than the pressure to be regulated, especially the present position of the object, such as the inclination.

BACKGROUND OF THE INVENTION

Hydrocephalus is a condition that is also sometimes known as "water on the brain". People with this condition have abnormal accumulation of cerebrospinal fluid (CSF) in the spine and ventricles, or cavities, of the brain. This may cause increased intracranial pressure inside the skull and progressive enlargement of the head, convulsion, and mental disability. The elevated intracranial pressure may cause compression of the brain, leading to brain damage and other complications.

Hydrocephalus is usually caused by a blockage of CSF outflow in the ventricles or in the subarachnoid space over the brain. The condition is called internal hydrocephalus and it results in increased CSF pressure. The production of CSF continues, even when the passages that normally allow it to exit the brain are blocked. Consequently, fluid builds inside the brain causing pressure that compresses the nervous tissue and dilates the ventricles. Compression of the nervous tissue usually results in irreversible brain damage. If the skull bones are not completely ossified when the hydrocephalus occurs, the pressure may also severely enlarge the head. In a normal healthy person, CSF continuously circulates through the brain and its ventricles and the spinal cord and is continuously drained away into the circulatory system. In a hydrocephalic situation, the fluid accumulates in the ventricles, and the skull may become enlarged because of the great volume of fluid pressing against the brain and skull. Alternatively, the condition may result from an overproduction of the CSF fluid, from a congenital malformation blocking normal drainage of the fluid, or from complications of head injuries or infections.

Internal hydrocephalus can be successfully treated by placing a drainage tube (shunt) between the brain ventricles and the abdominal cavity to eliminate the high internal pressures.

It involves the placement of a ventricular catheter into the cerebral ventricles to bypass the flow obstruction and drain the excess fluid into other body cavities, from where it can be reabsorbed. Most shunts drain the fluid into the peritoneal cavity (ventriculo-peritoneal shunt, or VP shunt), but alternative sites include the right atrium (ventriculo-atrial shunt), pleural cavity (ventriculo-pleural shunt), and gallbladder. A shunt system can also be placed in the lumbar space of the spine and have the CSF redirected to the peritoneal cavity (LP Shunt).

Shunt systems are usually also designed to function using the pressure differential between the brain and another part of the body and to regulate the drainage flow using a programmable valve. With the VP shunt, a surgical procedure provides an opening in the skull through which an entry catheter is introduced and passed through the brain tissue into the ventricles. The catheter is attached to a pump or valve, which is positioned subcutaneously against the exterior of the skull, to control fluid flow. A second exit catheter, usually also subcutaneous in position, is also attached to the pump and leads to the peritoneal cavity.

One example of such a shunt is described in US2004082900 concerning a cerebral spinal fluid (CSF) shunt comprising a ventricular cavity for receiving CSF in a drainage chamber for passing the CSF to a patient's abdominal cavity. An anti-syphon valve controls CSF flow from the ventricular cavity to the drainage chamber. The valve utilizes a thin, flexible portion of the ventricular cavity which operates an underlying pressure control membrane. The membrane overlies a valve opening that permits CSF flow from the ventricular cavity into the drainage chamber. In place of the membrane, a spring-biased ball can be used to open and close the valve opening.

Another example is US2004068201 describing devices and methods for removing cerebrospinal fluid (CSF) from a CSF space of a patient at relatively constant flow rates for patients having normal intracranial pressures, e.g. patients not suffering from hydrocephalus. The devices and methods provide drainage paths which permit the removal of CSF at relatively low flow rates, usually below 0.2 ml/day, at normal intracranial pressures, e.g. an intracranial pressure between −170 mm of H2O in upright patients and 200 mm of H2O in reclining patients. The system operates by externally receiving an output signal from a flow sensor in a flow lumen of the implanted CSF drainage shunt, said signal being representative of CSF flow through the flow lumen, wherein the flow sensor is selected from the group consisting of a thermal device, a dye release device, a differential pressure measuring device, a turbine meter, an angular momentum measuring device, a positive displacement measuring device, and an accumulator.

The document DE19541377A1 describes a valve unit that is located within a drainage channel to the head of the patient and contains two pressure controlled valves. The high pressure valve opens at a (programmable) pressure of say 40 cm of water, whilst the low pressure valve opens at a fixed pressure of 13 cm of water. In series with the low pressure valve and parallel to the high pressure valve is a position switch which, when the patient is standing (presenting an angle between 0 deg. and 45 deg.), closes the channel which is parallel to the high pressure valve. With the patient lying down, (angles between 45 deg. and 90 deg.) the drainage channel opens. The position switch comprises a pendulum and a valve seat which is closed by the pendulum. The pendulum is a ball (6) with an eccentric weight (8) which is located within a hollow area (10) within a housing (9). The pendulum can swing in every direction. The valve is connected to a circular channel (7) in the housing and the ball has channels (11) located in it as well. When the patient is upright the pendulum moves to ensure that the channels in the ball are sealed and thus the valve is closed. When the patient lies down, the channels in the ball connect to the circular channel whose outlet (13) leads to the drainage channel. The high pressure valve is bridged and the low pressure valve can operate.

None of these documents, however, describes that a number of factors would influence the intracranial pressure, such as the position and the activity of the person.

SUMMARY OF THE INVENTION

The present invention therefore aims to take other factors into account, where the main embodiment concerns including an inclination sensor to measure the present position of a person, and thereby anticipate increases in the pressure not related to e.g. cerebrospinal fluid (CSF). Such inclination sensors are well known in the art, and are for example widely used in vehicles.

One document WO03057016 discloses a system for non-invasively monitoring the operation and performance of an implanted cerebrospinal shunting system, where the system comprises an implanted controller; said controller further comprising: an inclination sensor; a pressure sensor; a wireless transceiver capable of communicating with an external programmer; and an embedded microprocessor, capable of reading said inclination sensor and said pressure sensor and transmitting, using said wireless transceiver, said readings from said sensors; and an external programmer with wireless capability, said programmer capable of wireless communication with said controller. A battery is embedded for running the devices.

It is an object of the present invention to introduce a system where no energy or power sources are implanted, any implanted systems being operated by externally transferred energy. This gives major advantages in that there is no need to make more than one surgical operation is needed for implantation the devices of the present invention. Furthermore, the lifetime of the device is indefinitive since the energy is supplied wireless by an external source without penetrating the skin. Therefor the risk of infection is minimal when compared to the current methods to measure the ICP of patients.

It is an object of the invention to improve the quality of measurements of such a dynamical physical parameter like the pressure for regulatory purposes.

In a first preferred embodiment of the invention measurement is improved by introducing a system to regulate physical parameter(s) where the system includes a sensor to measure a position or posture such as an inclination, angle or altitude.

In a further preferred embodiment the system is for regulating the pressure of a fluid inside a hollow object having a fluid outlet, the system comprising device(s) to regulate the fluid, a pressure sensor to measure the pressure of the fluid and the sensor to measure a position or postures of the object, such as the inclination, the angle or the altitude of the object.

In a further preferred embodiment of the invention, the object is a part of an animal or human body such as the head, and the pressure is the intracranial pressure.

The system would preferably comprise a receiving unit to receive signals from the sensors, and a transmitting unit to excite, instruct and/or to energize the sensors.

In a more advanced preferred embodiment of the invention further sensor(s) are included to the system measuring such parameters as the external and/or internal temperature and/or the barometer state.

In order to safely connect the parts of the system in relation to a person, then in a preferred embodiment the pressure sensor and/or the receiving unit and/or the transmitting unit is positioned in a bore in the scull and/or is inline with a shunt or catheter system, or alternatively some of or all the sensor(s) are positioned inside or at the wall of a vessel. Alternatively in another preferred embodiment of the invention, at least some of the sensors are 'floating' freely in the intracranial fluid.

To ensure easy attaching and detaching of units, especially the receiving and/or transmitting units, at the correct positions, in a further preferred embodiment of the invention magnetic element(s) are implanted beneath the skin of a person or an animal, and the units and/or the comprised parts being attracted by the magnetic elements to attach them to the correct positions.

In one preferred embodiment of the invention, the pressure sensor comprises a hollow casing having a opening, where one opening is covered by a diaphragm, and where the inside of the hollow casing comprises a magnetic field generating element at the surface of the diaphragm facing the inside of the hollow casing and a circuit comprising a capacitor and a coil.

An alternative use of the system of the invention is to survey and estimate the pressure load on parts of the body of a human being or an animal, such as the joints, the knees, the tissue and/or the organs.

A further advantage of the present invention is that medical staff may survey or track the body position or posture of a patient from remote locations.

BRIEF DESCRIPTION OF THE DRAWINGS

FIGS. 11C and 11D show two such angles of the head.

DETAILED DESCRIPTION OF THE PREFERRED EMBODIMENTS

Figure 1:
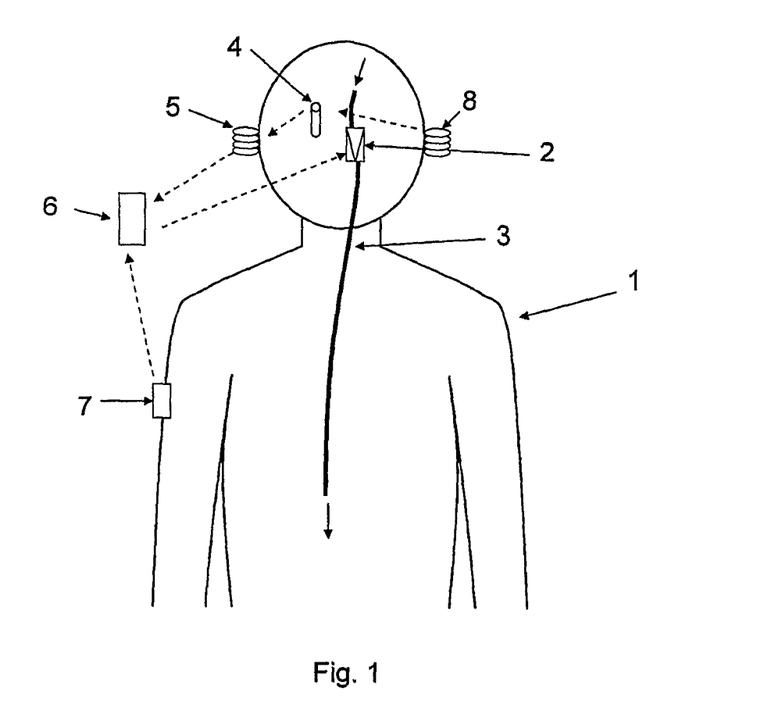
FIG. 1 shows the parts of the present invention.

FIG. 1 is a simple illustration of the basics of the system, where a drainage system comprising a valve or shunt system (2) and a tubing system (3) is placed in a person (1) for removing cerebrospinal fluid from a CSF space in the brain. The system comprises any tubing system (3) as known in the art for removing CSF to either another position within the body of the person, like the abdominal, or alternatively removing it totally from the body. The valve or shunt system (2) may be of any kind known in the art, such as it is described in e.g. US2004068201, and could comprise sensors like flow sensors and/or pumping mechanisms for actively helping to drain CSF from the brain.

A pressure sensor (4) is positioned to measure the intracranial pressure in preferably a CSF space. It may either be totally implanted beneath the skull or may be inserted in a small bore in the skull, or could be inline with a shunt or catheter system. It may communicate with the externals either by wires penetrating the skull, or more preferable wireless in any known manner.

A receiving unit (5), or antenna, is in one preferred embodiment positioned externally to the person (1), possible almost unnoticeable positioned behind an ear. The receiving unit (5) receives signals from the pressure sensor (4) relating to the intracranial pressure. The receiving unit (5) and the pressure sensor (4) could optionally be connected by wire, or operate wireless where one embodiment shall be discussed below. Depending on the embodiment of the invention, a transmitting unit (8) additionally is included to the system sending off signals, sonic energy or electromagnetic fields to the pressure sensor (4) as shall be described below. The transmitting unit (8) could be positioned as the receiving unit (5), and they could optionally be made as a combined transmitting/receiving unit.

In the preferred embodiment of the invention one or more sensors (7) is/are connected to the system and optionally attached to or implanted in the person (1). Such sensors would comprise an inclination sensor as they are known in the art, determining the present position status of the person (1), but could optionally additionally comprise other sensors too, such as temperature or barometric sensors.

In the preferred embodiment of the invention a processing system (6) receives and processes data from the receiving unit (5), the sensor(s) (7) and possible sensors in the drainage system (2, 3) relating for example to the flow in the tubing system (3). All these data are the processed to determine whether the draining rate is to be raised or lowered, or completely stopped, by adding data other than the CSF that still would influence the intracranial pressure, thereby raises or decreases in pressure that should not affect the drainage rate could be determined and anticipated.

Figure 2:
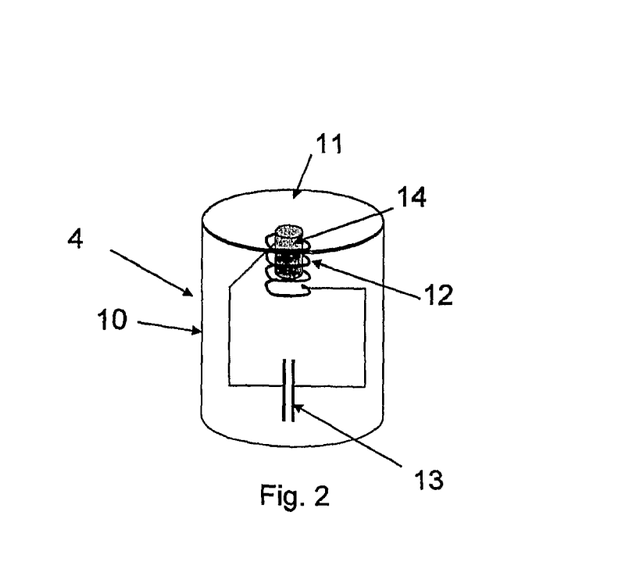
FIG. 2 shows a preferred pressure sensor of the invention.

FIG. 2 shows a simple example of a preferred pressure sensor (4) of the present invention. The sensor consists of a casing (10) having at least one opening from the internal volume of the casing (10) to the externals, where the opening is covered by a flexible and or bendable element (11) like a membrane or diaphragm. In the following the element is referred to as the diaphragm (11). The inside of the casing comprises a variable resonance frequency resonant LC-circuit as known from, for example, RFID tags comprising a coil, or inductor, (12), and a capacitor (13) in series (as illustrated) or in parallel. Attached to the surface of the diaphragm (11) facing the inside volume of the casing (10) is a magnetic element (14). The magnetic element (14) and the coil (12) are arranged in such a manner that the magnetic element (14) in response to deflection of the diaphragm occupies the space inside the coil (12) more or less influencing the natural frequency of the resonant circuit accordingly.

Figure 3A:
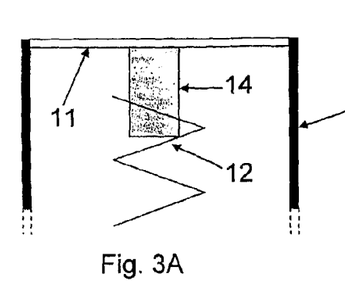
FIGS. 3A & B shows how the pressure sensor operates.
Figure 3B:
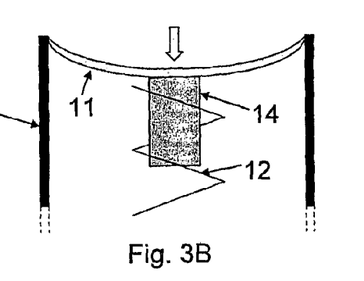

FIG. 3A shows a part of the pressure sensor (4) with an un-deflected diaphragm (11) where only a small section of the magnetic element (14) is surrounded by the coil (12), giving the resonant circuit a first natural frequency. FIG. 3B shows the same system where a pressure gradient has deflected the diaphragm into the internal of the casing (10) thereby moving a larger portion of the magnetic element (14) to be surrounded by the coil (12) changing the natural frequency of the resonant circuit. If the external pressure is lower than the internal pressure of the casing, the diaphragm would deflect outwards redrawing parts of the magnetic element (14) from occupying the space inside the coil (12).

During operation the resonant circuit is excited by the transmitting unit (8) inducing e.g. an electromagnetic field varying in frequency in order to 'scan' a range of frequencies. When the frequency of the induced electromagnetic field matches the resonance frequency, or natural frequency, of the resonant circuit, then it starts 'ringing', thereby generating and emitting a signal at the resonance frequency. This emitted signal will be received by the receiving unit or antenna (5) which thereby notes that the resonance frequency of the resonant circuit has been matched.

The advantage of this system is that no energy source would have to be attached to pressure sensor (4), all the needed energy would then be supplied from the externals, the resonant circuit being an inactive circuit. It is to be understood, however, that any known pressure sensor also would apply to the invention, like silicon pressure sensors. Alternatively energy could be stored by battery, being supplied from the externals by wire or being supplied by for example sonic or electro-magnetic waves and stored in reservoirs like inductors/coils or capacitors, like super capacitors, the resonant circuit then being an active circuit. The pressure sensor (4) and the resonant circuit could optionally be equipped with additional equipment and sensors, such as an inclination sensor, flow sensor, and temperature sensor, a micro chip for processing data etc.

Figure 4A:
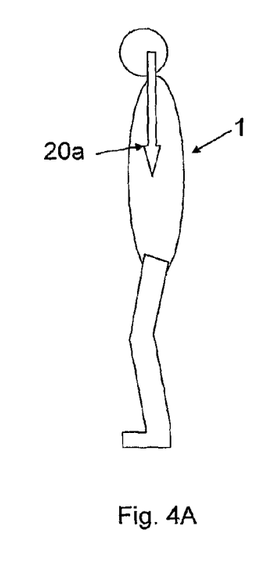
FIGS. 4A & B illustrates relevance of body position to intracranial pressure.
Figure 4B:
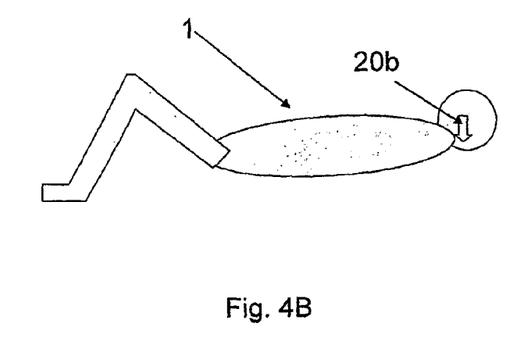

FIGS. 4A and 4B show two positions of a person (1), where the gravity (20a) to be overcome of the circulatory system of the standing person (1) in FIG. 4a is substantially larger than the gravity (20b) of the person (1) lying down in FIG. 4B. A traditional system might then over-drain when the person (1) is standing, and under-drain when the person (1) is e.g. lying down. An inclination sensor attached to the person (1) would sense the present position of the person making it possible to anticipate raising or decreasing pressures due to this, and thus regulate the drainage rate accordingly.

Figure 5:
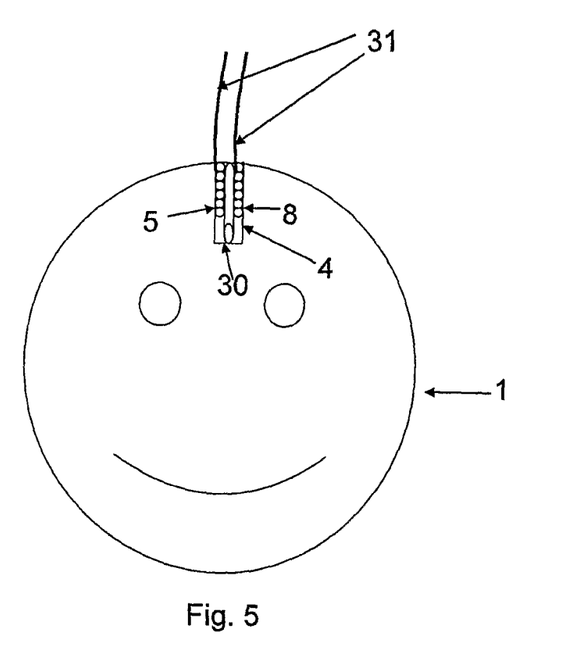
FIG. 5 shows parts of the present invention inserted into a bore in the scull.

FIG. 5 shows an illustration of an embodiment where the transmitting unit (8), receiving unit (5) and the pressure sensor (4) are inserted into a bore (30) in the skull. Such a bore (30) may have a diameter in the range from 1-30 mm, and both the receiving unit (5) and transmitting unit (8) could be constructed as a twisted pair of wires having diameters in the ranges from 0.01-15 mm, and the pressure sensor (4) could be constructed with a diameter in the range from 0.1-30 mm, so the bore would have a sufficient size to comprise all three units, pressure sensor (4), transmitting unit (8) and receiving unit (5). The units could then communicate with each other and the externals by wire or wireless, and could be coupled to external power sources, like batteries, with wires (31).

Sensors (7), such as the inclination sensor, could be external to the person (1), or could be implanted inside the person, in the head or other body parts, possibly subcutaneous.

Figure 6:
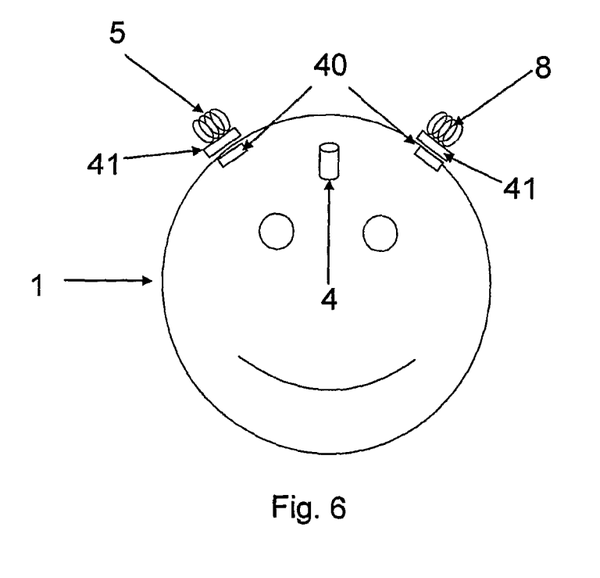
FIG. 6 shows magnetic field generating elements implanted under the skin for attaching antennas.

FIG. 6 shows an embodiment of the invention where one or more magnetic field generating elements (40) (preferably standard permanent paramagnetic or ferromagnetic magnets), or just magnetic elements (40), are implanted just beneath the skin of a person. The receiving unit (5) and/or transmitting unit (8) could then be equipped with parts (41) being attracted by the magnetic elements (40). This would fix the units (5) and (8) to well defined positions at the person (1) and would define the positions of the external units relative to the implanted ones, like the pressure sensor (4). Such well defined positions of the receiving units (5) and/or the transmitting units (8) ensure repeatability of the measurements, and it makes it easy to detach and attach the units (5) and (8), for instance when the person (1) is taking a bath.

The magnetic elements (40) could advantageously be ferrites having known positions and orientations within the body. This especially would be relevant for MRI-scans to avoid a possible de-magnetization of the magnetic elements (40), since knowing the orientation of them would make it possible to position the person (1) at a specific orientation in the MRI scanning equipment to avoid such a de-magnetization. This is a real risk, since such scans are the common way to survey the draining and shunting systems (2, 3) for clogging and the like.

Figure 7:
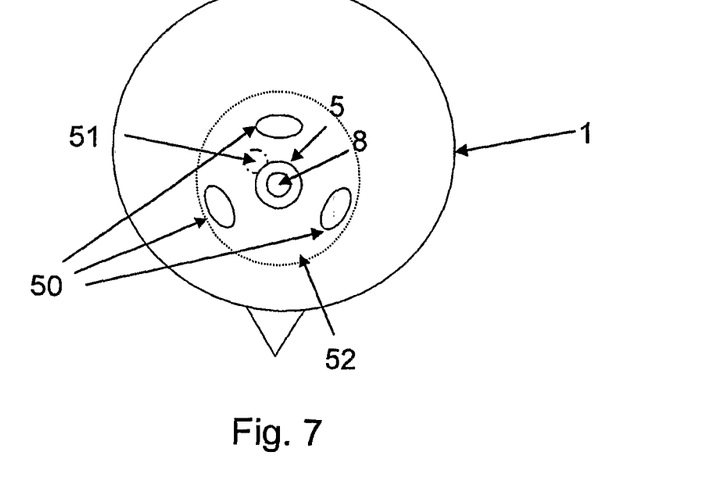
FIG. 7 illustrates a further embodiment of the present invention.

FIG. 7 illustrates a further more advanced embodiment of the present invention, showing the receiving unit (5) (and/or also including the transmitting unit (8), in the following embodiments however just being referred to as the receiving unit (5)) and sensor or sensors (51), where the sensor or sensors (51) could include any numbers and kinds of sensors and permutation of such, but in the main embodiment includes the pressure sensor (4) and optionally one or all of an inclination sensor, a temperature sensor, a flow sensor, and a barometric sensor.

Further seen is three aid receiving (and/or transmitting) units (50) positioned in a configuration with the receiving unit (5) in the center of the construction. Such a structure of at least three sensors (in any numbers and permutation of receiving units (5) and aid receiving units (50)) makes it possible to obtain a substantially 3-D 'picture' or view of the position of the sensor or sensors (51) by comparing the field strengths measured by the receiving units (5, 50), or at least getting an indication of the position and/or radial orientation of the sensor or sensors such as the pressure sensor (50) Any number of aid receiving units (50) could be introduced, and they could be constructed in any manner known in the art, preferable as the receiving unit (5). They could preferable also be attached to a person (1) in the same manner as the receiving unit (5) and/or transmitting unit (8).

Such a setup with at least one receiving unit (5)(and/or transmitting unit (8)) with at least one, but preferable two or even more preferred three or more receiving (and/or transmitting) units (50), is the following being referred to as the antenna system (52), where the units (5, 8, 50) are preferably connected and fixed to each other, possibly by attaching them to some platform (53) (optionally flexible) like a headgear (54) such as a cap/showercap.

Figure 8:
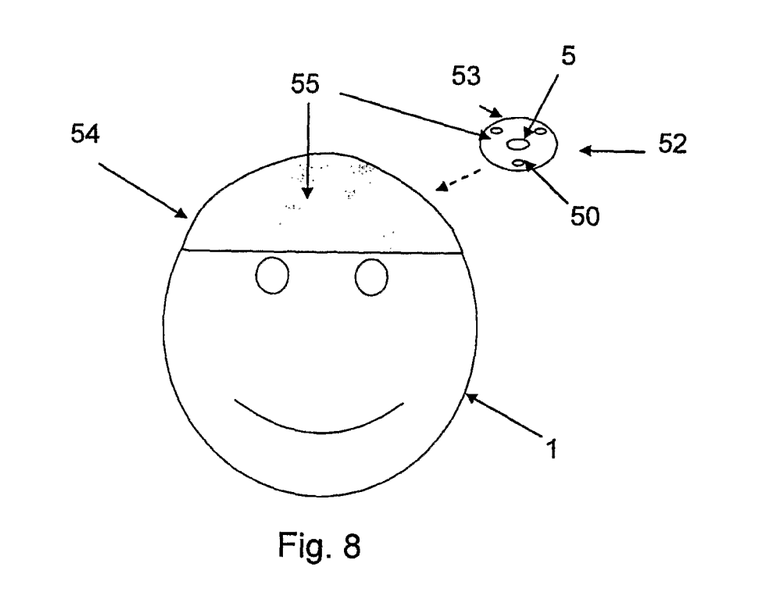
FIG. 8 shows another embodiment of the present invention.

In one not limiting embodiment shown in of the present invention shown in FIG. 8, the person wears such a headgear (54) like a cap, and the antenna system (52) is attached to each other or an optionally flexible platform (53), where one or both of the headgear (54) and the antenna system (52) or optionally flexible platform (53) comprises a VELCRO® brand hook-and-loop fastener surface (55), making it easy to attach and detach the antenna system (52) or optionally flexible platform (53) to the headgear (54). If the surface of the headgear (54) is of a VELCRO® brand hook-and-loop fastener surface it would be an advantage to cover this with a second headgear, cap, hat or the like, to avoid the VELCRO® brand hook-and-loop fastener surface from 'collecting' undesired elements.

Figure 9A:
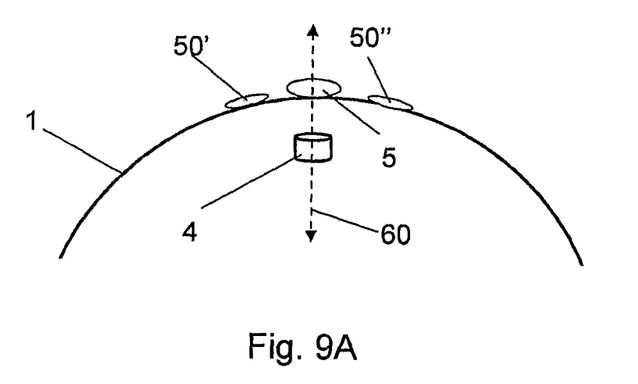
FIGS. 9A and 9B show a top of a scull or head of a person where a sensor such as a pressure sensor is implanted having a present radial direction or orientation.
Figure 9B:
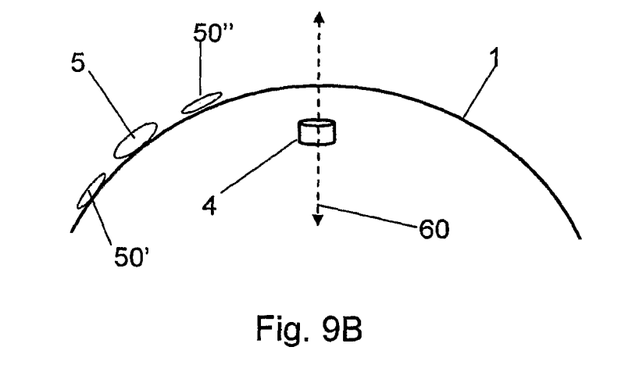

FIGS. 9A and 9B shows the top of a skull or head of a person (1), where a sensor such as a pressure sensor (4) is implanted having a present radial direction or orientation. The relative angular radial orientation of the sensor to the receiving units (5, 50) and/or transmitting units (8) strongly affects the strength of the signal being measured by the receiving units (5, 50). The angular directions of the best signal are indicated by arrows (60), and FIG. 9A shows the situation where the receiving unit (5) is positioned at this angular direction, in the shown illustration also being the position with the shortest distance to the sensor (4), the two seen aid receiving units (50') and (50") being at substantially similar angular directions and distances to the sensor (4), thus measuring substantially the same signal strengths. FIG. 9B, however, shows a situation where neither of the receiving units (5, 50) is at the best angular distance (60). In this situation the aid receiving unit (50") would measure the strongest signal.

For many persons (1) it is not critical thy wear the antenna system (52) at all times, it may be removed when taking a bath etc. Since the control system of the drainage system (2, 3) is calibrated to the present conditions, it is essential to ensure a substantially consequence and continuation in the attachment of the antenna system (52). Otherwise it could lead to failures in the regulation.

Figure 10:
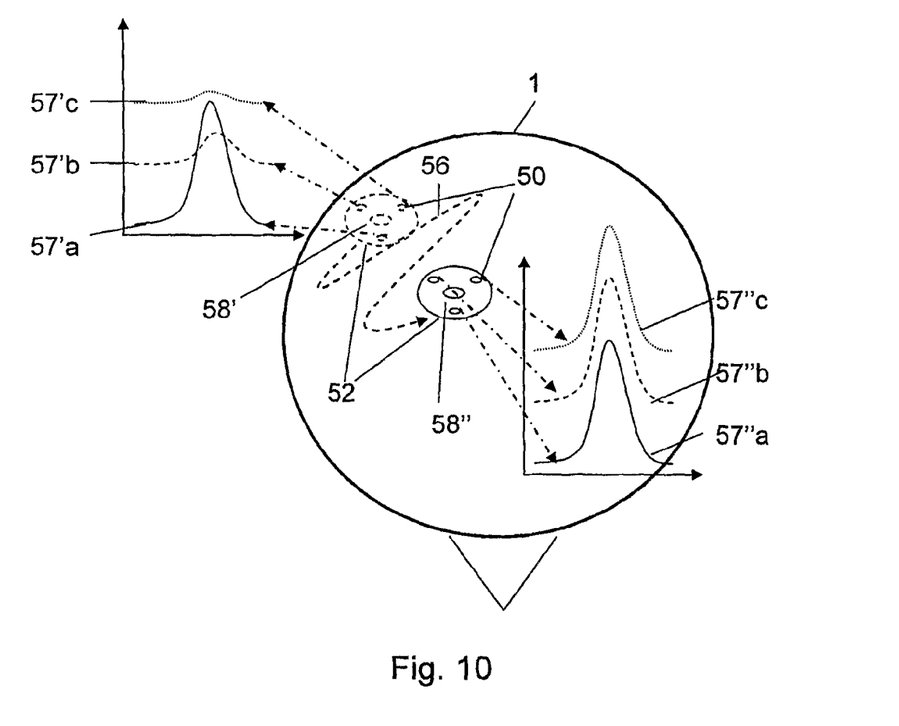
FIG. 10 illustrates how an antenna system is attached to the head for measurements at a position ensuring a substantually consistent and strong signal even after the antenna system has been detached and attached multiple times.

FIG. 10 illustrates how the aid receiving (50) of the antenna system (52) are used to attach the antenna system (52) to the head for measurements at a position ensuring a substantially consistent and strong signal even after the antenna system (52) has been detached and attached a plural of times. This is also relevant for the relation of the measurements to the data obtained by the inclination sensor (7).

By sweeping (56) the antenna system (52) over the head a set of changing signals (57a, 57b, 57c) are measured by the aid receiving units (50), where the figure illustrates a set of signals (57a', 57b', 57c') at a first position (58') of the antenna system (52), where the signals are significantly different with only the signal (57a') being strong. At the position (58'), however, all three signals (57a", 57b", 57c") are substantially equally strong, indicating the main receiving unit (4) is positioned at a position with a strong signal. Each of the signals (57a-c) for example could be visualised to the person (1) in a simple two-state manner, where a 'no-good' signal changes to a 'good' signal when the strength exceeds a defined threshold value. A sufficient good position (58) has then been found with a full set of 'good' signals. This could for example being light signals changing from red to green on a display.

Figure 11A:
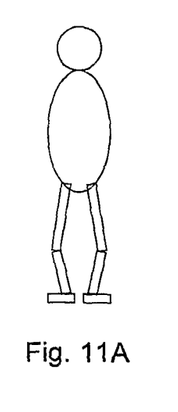
FIGS. 11A-D illustrate a calibration procedure, where measurements are made with a person in a number of different positions, such as standing as in FIG. 11A, sitting as in FIG. 11B, and lying with the head in a number different angles, where
Figure 11B:
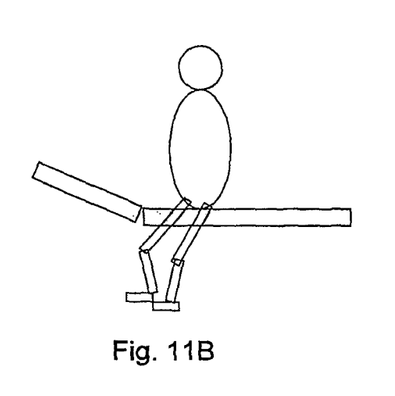
Figure 11C:
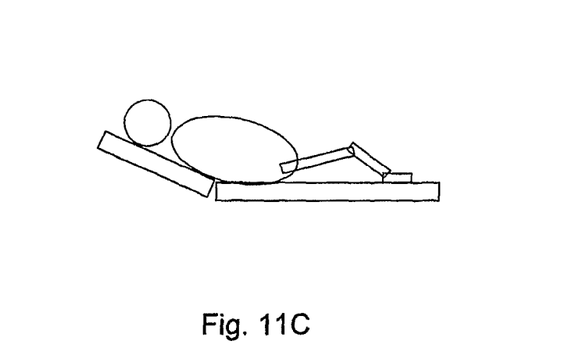
Figure 11D:
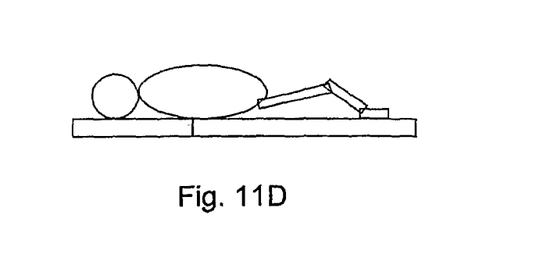

Over time the conditions of and around the sensor (4) may change due to a plural of reasons, such as aging of the sensor (4), substances depositing at or around the sensor (4), minute changes in the position etc., so it is essential for the pressure readings or measurements by the pressure sensor (4) to be set or calibrated in relationship to the inclination of the patients head from time to time. FIG. 11A-D illustrates such a calibration procedure, where measurements are made with the person (1) in a number of different positions, such as standing as in FIG. 11A, sitting as in FIG. 11B, and lying with the head in a number different angles, where FIGS. 11C and 11D shows two such angles of the head. The data measured with the receiving units (5, 50) then are compared with the data obtained with especially the inclination sensor (7), but optionally also with the other sensors present in the system, such as a temperature sensor.

Of further advantages of the construction the antenna system (52), or just aid antennas (50), is they on a daily basis also helps improving the measurements in that they covers an area of sensors, so minute variations in position of for example the pressure sensor (4) may be corrected by help of the aid antennas (50).

In one embodiment the inclination sensor (7) is included into the antenna system (52).

In one not limiting but preferred embodiment, the pressure sensor (4), as also described above, is located in or through a bore in the skull, either epidural or subdural, above and in touch with the dura covering the brain, or below the dura, etc. Other sensors, such as, but not excluded to, a temperature sensor could with advantage be positioned.

In one further advanced embodiment of the present invention, the system introduces a complete set of implanted devices being supplied with externally transferred power, no battery or the like being implanted. This has already been introduced by the described pressure sensor, but may be introduced to the shunt device too.

Wireless energy transfer is a well known technology, and comprises such as by induction, radio and microwave, laser, electrical conduction etc.

As one example is resonant induction, using the "electrodynamic inductive effect" or "resonant inductive coupling", where for example a primary coil generates a predominantly magnetic field inducing current in a secondary coil being within the field.

Since the early 1960s such resonant inductive wireless energy transfer has successfully been utilized in implantable medical devices, including such devices as pacemakers and artificial hearts. While the early systems used a resonant receiver coil, later systems implemented resonant transmitter coils as well.

Today resonant inductive energy transfer is regularly used for providing electric power in many commercially available medical implantable devices.

In this manner it is possible to operate the devices, such as the sensor (4) and the device(s) (2, 3), by wireless transmitted energy, this energy being sufficient to provide the energy to the systems, making it unnecessary to introduce a power supply such as a battery into the body, even the devices are totally implanted into the body.

For example, a valve in the shunt could be opened by magnets or IC-circuits with a different natural frequency than the pressure sensor, the valve then being activated and powered via the transmitters of the system.

For example a pulse from a transmitter activates and opens the valve, the valve having a slow or 'delayed' closing time, so that repeated pulses at specified intervals keeps the valve at an open state.

In even a further advanced embodiment of the present invention, more than one pressure sensor could are introduced/implanted, for example the one in the CSF space as described above, and a further pressure sensor at a position or location where the pressure is not influenced directly by hydrocephalus, but is influenced by activity, inclination, altitude etc. of the person. Such an extra pressure sensor could be used both for calibration purposes, but also as a further indication of those being pressure changes due to hydrocephalus, and those not.

As an example, the further pressure sensor(s) is introduced in the cavity where to the CFS fluid is drained. This also offers the possibility, that the readings from the different sensors may be compared and be used in the regulation of the drainage system (2, 3), in that a pressure difference, or pressure gradient, over the drainage system (2, 3), is established. The flow rate, or simply just the drainage, may then be controlled or regulated in dependence of this pressure different or gradient.

In a further embodiment of the present invention, the pressure gradient over the drainage system (2, 3) is used to generate energy for the system by introducing a small generator in the drainage system (2, 3), and possible introducing a energy storage being supplied with energy from the small generator.

While the present invention has been illustrated and described with respect to a particular embodiment thereof, it should be appreciated by those of ordinary skill in the art that various modifications to this invention may be made without departing from the spirit and scope of the present.

What is claimed is:

1. A system to regulate physical parameter(s) where the system includes a first sensor to measure a position, a second sensor to measure the pressure of a fluid and implanted means to receive wireless transmitted energy;
   wherein the second sensor operates by wireless transmitted energy; and
   wherein the system further includes an antenna system comprising at least one receiving unit, at least one transmitting unit and at least three aid receiving units, the at least one receiving unit and the at least three aid receiving units forming a construction with the at least one receiving unit arranged in the center of the construction, the antenna system thereby allowing the at least one receiving unit to be positioned at a position with a strong signal, based on comparison of the field strengths of signals received by the at least three aid receiving units.

2. The system according to claim 1, wherein the physical parameter to be regulated is a pressure, and the first sensor is measuring inclination, angle or altitude.

3. The system according to claim 2, wherein the pressure is the pressure of a fluid inside a hollow object having a fluid outlet, the system comprising device(s) to regulate the fluid, wherein the first sensor to measure the position is measuring the inclination, the angle or the altitude of the hollow object, and wherein the device(s) operate by wireless transmitted energy.

4. The system according to claim 3, wherein the hollow object is a part of an animal or human body.

5. The system according to claim 4, wherein the hollow object is the head, and the pressure is the intracranial pressure.

6. The system according to claim 5, wherein the system further comprises at least one additional sensor measuring at least one of an external temperature, an internal temperature and a barometer state.

7. The system according to claim 5, wherein at least one of the pressure sensor, the receiving unit, and the transmitting unit are adapted to be positioned in a bore in the skull.

8. The system according to claim 5, wherein the position sensor is positioned inside or at the wall of a vessel.

9. The system according to claim 1, wherein the system further includes a sensor measuring the blood pressure inside a blood vessel.

10. The system according to claim 5, wherein at least one magnetic element is implanted beneath the skin, and at least one of the receiving unit and the transmitting unit comprise parts being attracted by the at least one magnetic element.

11. The system according to claim 2, wherein the sensor measuring the inclination, the angle or the altitude is implanted into the body of an animal or a human being.

12. The system of claim 3, wherein the pressure sensor comprises a hollow casing having an opening, where the opening is covered by a diaphragm, and where the inside of the hollow casing comprises a magnetic field generating element at the surface of the diaphragm facing the inside of the hollow casing and a circuit comprising a capacitor and a coil.

13. The system according to claim 1, wherein the physical parameter to be regulated is a pressure load on parts of the body of a human being or an animal.

14. The system according to claim 1, wherein at least one of the pressure sensor, the receiving unit, and the transmitting unit are inline with a shunt or catheter system.

* * * * *